United States Patent [19]
Lawson et al.

[11] Patent Number: 5,453,625
[45] Date of Patent: Sep. 26, 1995

[54] MULTIPLE LAYER CALIPER MEASUREMENTS USING PHOTOISOMERS

[75] Inventors: Del R. Lawson, Inver Grove Heights; Jeffrey A. Boettcher, Falcon Heights; Lanny L. Harklau, Stillwater, all of Minn.

[73] Assignee: Minnesota Mining and Manufacturing Company, St. Paul, Minn.

[21] Appl. No.: 193,599

[22] Filed: Feb. 8, 1994

[51] Int. Cl.⁶ ............................................. G01N 21/64
[52] U.S. Cl. ............... 250/459.1; 250/302; 250/458.1; 356/381
[58] Field of Search .................. 250/461.1, 458.1, 250/459.1, 302; 356/381

[56] References Cited

U.S. PATENT DOCUMENTS

| | | | |
|---|---|---|---|
| 3,341,705 | 9/1967 | Alburger | 250/302 |
| 3,956,630 | 5/1976 | Mellows | 250/461.1 |
| 4,250,382 | 2/1981 | Libby | 250/302 |
| 4,841,156 | 6/1989 | May et al. | 250/459.1 |

OTHER PUBLICATIONS

Takahide Minami et al., Picosecond Time–Resolved Fluorescence Spectroscopy of the Photochromic Reaction of Spiropyran in Langmuir–Blodgett Films; J. Phys. Chem., 95(10); pp. 3988–3993, 1991.

*Primary Examiner*—Carolyn E. Fields
*Attorney, Agent, or Firm*—Patterson & Keough

[57] ABSTRACT

A method and system is disclosed for measuring a functional characteristic of one or more thin film coatings applied to a thin film using a photoisomer. A photoisomer is mixed into each functional coating in known amounts. Photodetection of the photoisomer as a part of the functional coatings is used to control a functional characteristic of the thin film during the manufacturing process. The photoisomer is activated with light of a selected wavelength range, and light fluorescence is measured in another selected wavelength range.

12 Claims, 5 Drawing Sheets

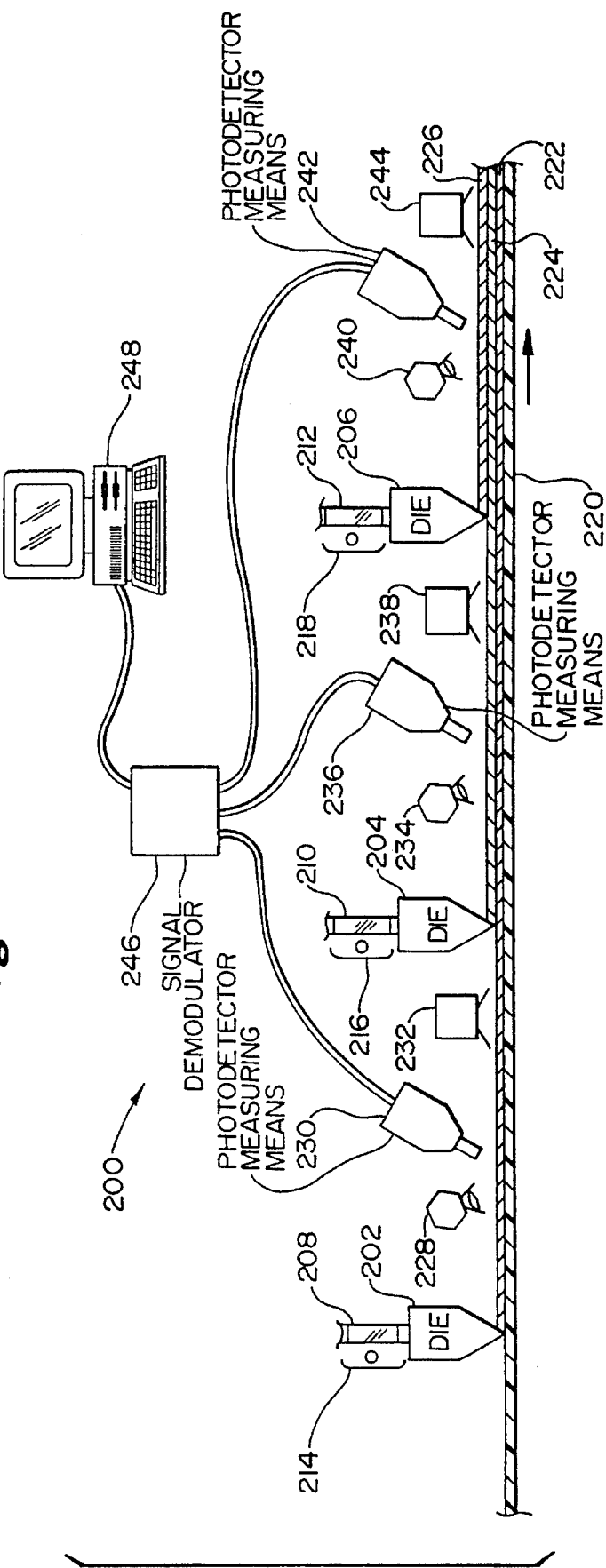

MULTIPLE LAYER CALIPER MEASUREMENTS USING PHOTOISOMERS

CROSS REFERENCE TO CO-PENDING APPLICATIONS

This invention is related to, and filed concurrently with, U.S. patent application Ser. No. 08/193,428 entitled FLUORESCENT SPECTRAL DIFFERENTIAL MEASUREMENT and assigned to the same assignee.

FIELD OF THE INVENTION

The invention relates generally to spectroscopic measurements of functional characteristics of thin films and particularly to exploiting the dual absorption spectra characteristics and fluorescent nature inherent to photoisomers.

BACKGROUND OF THE INVENTION

Caliper measurement of thin films and functional coatings applied to the thin films is important to the industry producing these products. Typically, the measurements involve removal of samples or representative pieces of the product from a production process. These systems include use of fluorescence, light absorbance, and physical measurement techniques. However, these techniques are limited to a single fluorescence or absorbance probe in a single functional coating or thin film. Many thin film products now have multiple functional coatings, often applied simultaneously. However, there is no method or apparatus for evaluating multiple functional coatings in an on-line manufacturing process where that manufacturing process is simultaneously applying multiple functional coatings onto a thin film.

SUMMARY OF THE PRESENT INVENTION

The present invention is a method and system for measuring a functional characteristic of one or more thin film coatings applied to a thin film using a photoisomer mixed in known amounts into each functional coating. The photoisomer is able to change between two absorption spectra when induced by light of an appropriate wavelength. While activated, the photoisomer undergoes light absorption or fluorescent light emission measurements. The degree of absorption or fluorescence is then used to calculate a functional characteristic of the functional coating applied as a layer to the thin film. The invention is particularly useful as an on-line measuring and monitoring system for the control of the manufacturing process of thin film coatings and as a measurement tool for quality assessment of the manufacturing process.

BRIEF DESCRIPTION OF THE DRAWINGS

FIG. 5b is a side cross sectional schematic view of the die depicted in FIG. 5a.

FIG. 8 is a side schematic view of another on-line embodiment of the invention.

DETAILED DESCRIPTION OF THE INVENTION

Figure 1:
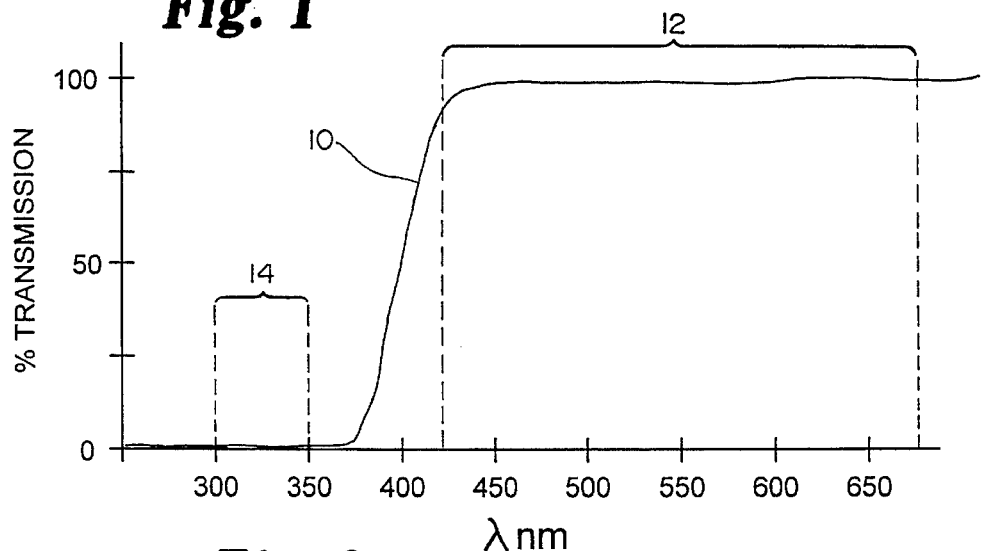
FIG. 1 is a graphic representation of a light transmission spectrum curve for the photoisomer 1,3',3'-trimethyl-6'-nitrospiro-(2-H'-1'-benzopyran-2-2'-indoline) (BIPS) in the deactivated state.

The invention relates to an on-line capability for accomplishing accurate measurements of thin films and functional coatings applied to thin films. Co-pending and commonly assigned U.S. patent application Ser. No. 08/193,428 uses a rapid change in the fluorescent spectrum of a fluorescent probe mixed within a functional coating to achieve on-line measurement capabilities. The probe discriminates from fluorescent competition of other fluorescent probes in other layers, fluorescing coating material or from the thin film the coatings are applied onto.

This invention exploits the dual absorption spectral characteristic and fluorescence of photoisomeric compounds. As used below, a photoisomer is a single chemical species that undergoes photochromism. Photochromism is a change, in a single chemical species, between two states having distinguishably different absorption spectra. The change in absorption spectrum is induced, in at least one direction, by the action of electromagnetic radiation. The appropriate inducing wavelength of light, when absorbed by a photoisomer alters the photoisomer from one isomeric state to another. This alteration, or activation, of the photoisomer by the first wavelength light, referred to as inducing wavelength range A, causes a change in the absorption spectrum of the photoisomer. Generally, this changes the absorption spectrum through a different wavelength range, referred to as Δ-absorption wavelength range B. This change in absorption can be either a decrease or an increase and is proportional to the amount of photoisomer present. The wavelength ranges of the inducing electromagnetic radiation as well as the Δ-absorption spectra are usually in the ultraviolet, visible, or infrared regions. The invention is not limited to a few photoisomers. Since the invention exploits the alteration in the absorption spectrum, any and all photoisomers are useful by the invention as probes in the functional coatings layered onto thin films.

The activation step, as noted above, involves the absorption of appropriate electromagnetic radiation energy to induce the photoisomer to change. This activation step of absorbing energy gets the photoisomer over the threshold separating the two isomeric states. Since the activation step involves the input of energy in order to reach the activated state, generally this activated state is less stable than the non-activated state and the photoisomer can revert back to the inactivated state with little or no additional energy requirement. However, the stability of an activated photoisomer is quantifiable and useful to the invention. For example, some photoisomers flip back and forth between a trans and cis configuration such as can occur in a carbon-carbon double bond. Other photoisomers undergo activation involving a reversible quasi-destruction of a chemical bond, such as homolytic cleavage, to change the absorption spectrum characteristic of this type of photoisomer. There are numerous suitable photoisomers, and a representative list includes such compounds as: stilbene; chrysene; 2-(2,4-dinitrobenzyl)pyridine; (diphenylthiocarbazono)phenylmercury; ethyl-bis-(2,4-dinitrophenyl)acetate; 1',3',3'-trimethylspiro-8-nitro(2H-1-benzopyran-2,2'-indoline); and 1,3',3'-trimethyl-6-hydroxyspiro-(2H-benzopyran-2,2'-indoline). Representative families of chemical photoisomers are the viologens, spiroxazines, fulgeides, and the fulgemides. The present invention is capable of taking advantage of the photoisomeric characteristic of virtually all photoisomers.

The activation of many photoisomers not only changes the absorption spectrum, but also changes the levels of fluorescence emissions. Useful levels of measurable fluorescence are usually seen in those photoisomers that demonstrate increased absorption changes in the Δ-absorption wavelength range B when in the activated or induced state. This increased absorption of light energy from Δ-absorption wavelength range B is emitted as fluorescence in a fluorescence wavelength range C. In this circumstance, this Δ-wavelength range B spectrum, when used as the source wavelength to illuminate the activated photoisomer, acts as an excitation wavelength range B. The intensity of the fluorescence is directly proportional to the amount of activated photoisomer present.

Also, light from the Δ-absorption wavelength range B, if used to scan a photoisomer that demonstrates increased absorption, will generally not only cause fluorescence in the fluorescence wavelength range C, but will also switch the photoisomer back to its alternate, more stable non-activated state.

FIG. 1 is a graphic representation of a light transmission spectrum curve 10 for the photoisomer 1,3',3'-trimethyl-6'-nitrospiro-(2-H'-1'-benzopyran-2-2'-indoline) (BIPS) in the deactivated state. BIPS is a compound from the spiroxazine family of photoisomers. BIPS undergoes a reversible chemical ring opening reaction.

As shown in FIG. 1, in wavelength range 12 there is virtually complete transmission of light through BIPS. Activation of BIPS is accomplished by using light in an inducing wavelength range A corresponding to a range of 250 nm to 350 nm. A portion of this inducing wavelength range A is included in FIG. 1 as wavelength range 14 which shows that there is little transmission of light through BIPS in this wavelength range, i.e. the light in the inducing wavelength range A is being absorbed. This light absorption is used to drive the photoisomeric process.

Activation of BIPS by light from the inducing wavelength range A leads to an increase in absorption in the Δ-absorption wavelength range B for BIPS due to the photoisomeric nature of BIPS. As shown by spectrum curve 16 in FIG. 2, the photoisomeric changes are evidenced by a decreased transmission of light in the Δ-absorption wavelength range B from approximately 500 nm to 650 nm and partially indicated by wavelength range 18 centered at 580 nm to 600 nm.

Figure 3:
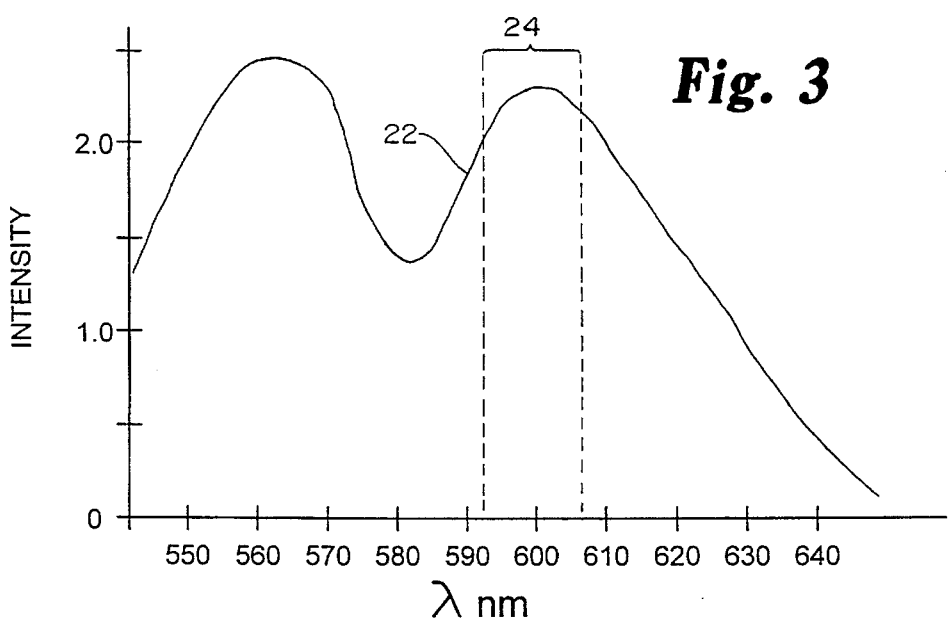
FIG. 3 is a graphic representation of a fluorescence emissions spectrum curve for the photoisomer 1,3',3'-trimethyl-6'-nitrospiro- (2-H'-1'-benzopyran-2-2'-indoline) (BIPS) in the activated state and excited by appropriate wavelength light.

Another change that occurs in BIPS with activation by light from inducing wavelength range A is fluorescence emissions in a fluorescence wavelength range C at approximately 550 nm to 640 nm when excited by light from Δ-absorption, or excitation wavelength range B. FIG. 3 depicts the fluorescence emissions spectrum curve 22 for BIPS when exposed to an excitation light of 500 nm. As shown, there is relatively intense emissions in wavelength range 24 centered at 600 nm. Non-activated BIPS does not demonstrate this fluorescent characteristic.

The invention is a method and system using the fluorescence or the change in absorption of an activated photoisomer as a measuring probe to determine a functional characteristic of a thin layer functional coating containing the photoisomer probe. Some examples of a functional characteristic of a thin layer functional coating are thickness, weight, and curing rate. After measuring the photoisomer probe in a functional coating layer, the probe can be promptly deactivated to not interfere with any subsequent measuring steps. The same photoisomer probe, mixed in as a part of several different functional coating layers, can be activated and then deactivated to accomplish measurement of each individual layer. Additionally, several different photoisomers may be used, one photoisomer added to each functional coating applied to the thin film.

The sequence of activation, measuring and deactivation of a photoisomer for each functional coating layer used in a manufacturing process allows for the continuous use of the same photoisomer probe in multiple layers coated on the same thin film. Using the same photoisomer for each layer simplifies the manufacturing process by eliminating the necessity of changing or adding additional activating light sources or detectors. This would be the preferred use. Alternatively, the use of multiple different photoisomers, one to each layer, provides for versatility in choice of chemical and physical characteristics between a probe and the layer it will be a part of, as well as a broad choice in light wavelengths for activation, absorption and fluorescence and deactivation.

Measuring the absorption of light and correlating the degree of absorption to concentration of the chemical causing the absorption follows Lambert's Law for absorption. This is a natural logarithmic relation between an amount of chemical present and the degree of absorption measured. Measuring the absorption of light in the Δ-absorption wavelength range B of an activated photoisomer probe yields the amount of photoisomer present using Lambert's Law. This method of measurement is not as sensitive as measuring fluorescence because of the logarithmic relationship and the fact that the light used to measure the absorption is also capable of deactivating the probe. As is the case for BIPS, one of the ways for effecting deactivation of BIPS is to use light from a source emitting in the Δ-absorption wavelength range B. Therefore, when absorption is used as the technique to determine the amount of BIPS present, the level of absorption is changing as a function of the time the activated photoisomer probe is exposed to the light from the Δ-absorption wavelength range B.

Measuring fluorescent emissions in a fluorescing wavelength range C is a preferred method. Fluorescence is linearly related to the amount of probe present and is therefore most sensitive to changes in concentration. Additionally, the amount of light needed from the Δ-absorption wavelength range B to excite fluorescence is substantially less than that needed to accomplish an absorption measurement, therefore the degree of error induced by deactivation becomes negligible by comparison. When the thin film is put into motion, as in an on-line manufacturing process, then new film is passing by the light source constantly. Such motion results in deactivation changes which are not apparent during measurements taken during production.

Figure 4:
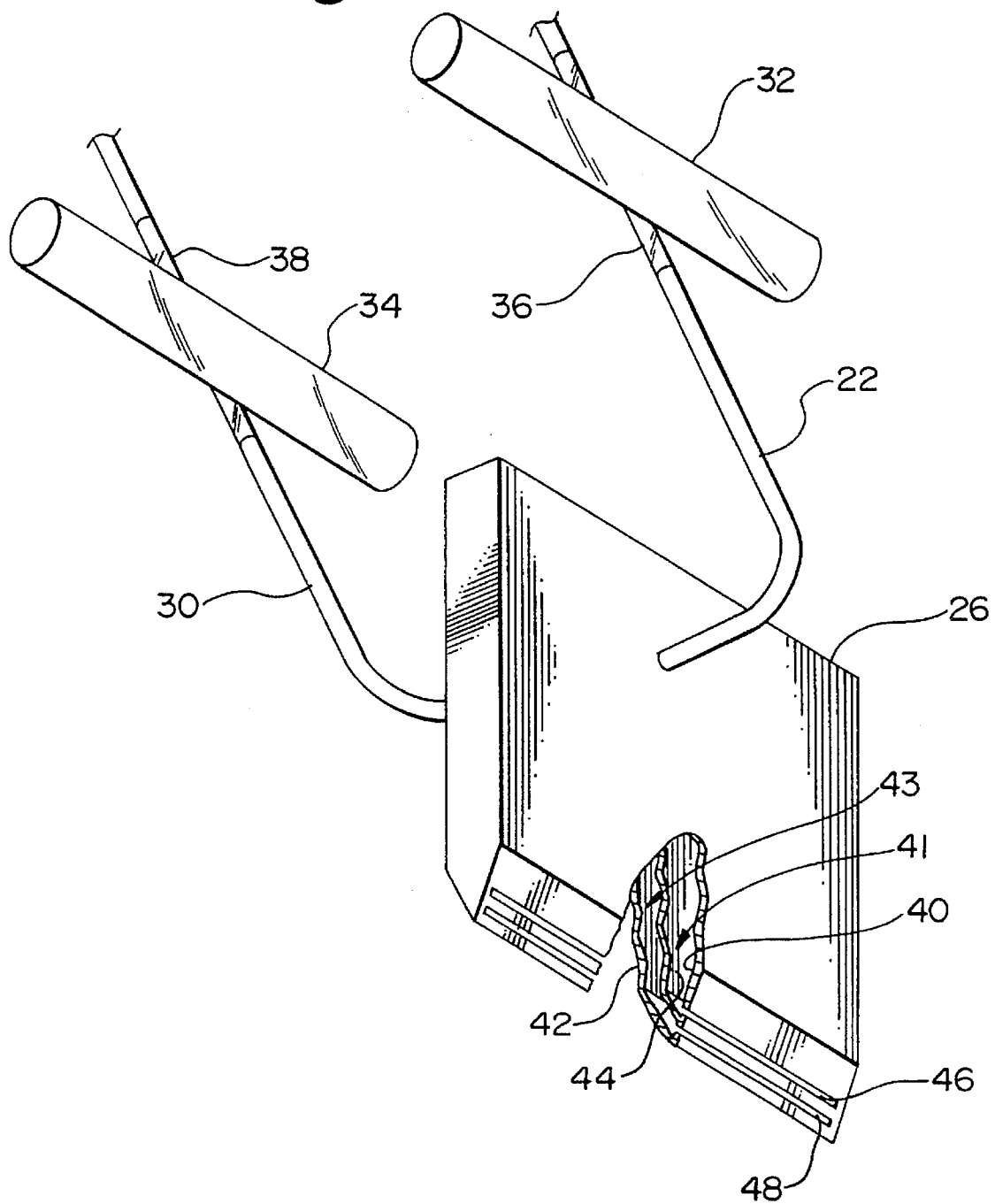
FIG. 4 is a perspective schematic view of a die used in the application of functional coatings onto thin films.

The application of functional coatings onto a thin film can use one or more dies to apply functional coatings. However, in this invention, examples of such dies are shown with the configurations of FIGS. 4, 5a and 5b. In FIG. 4, die 26 is configured to receive two liquid functional coatings via lines 28 and 30. Activation of the photoisomer probe in each functional coating is accomplished by sequentially turning on and off light sources 32 and 34 which direct their light through the appropriately transparent walls 36 and 38 of lines 28 and 30. As shown in FIG. 4, die 26 is constructed with two outer walls 40 and 42 separated into two chambers 41 and 43 by a divider 44. Outer walls 40, 42 meet at an apex with divider 44 to form two slit openings 46 and 48. The functional coating material supplied by lines 28, 30 are delivered to their respective chambers 41, 43. The contents of chamber 41 are extruded through die slit 46 with chamber 43 ending in die slit 48.

Figure 5A:
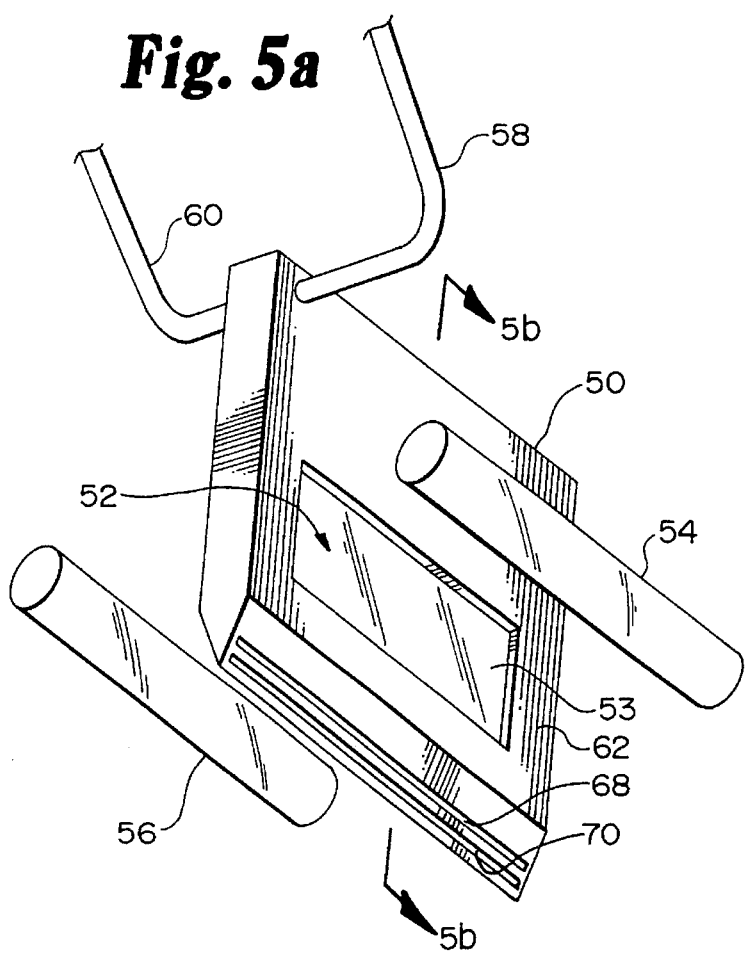
FIG. 5a is a perspective schematic view of another type of die used in the application of functional coatings onto thin films.
Figure 5B:
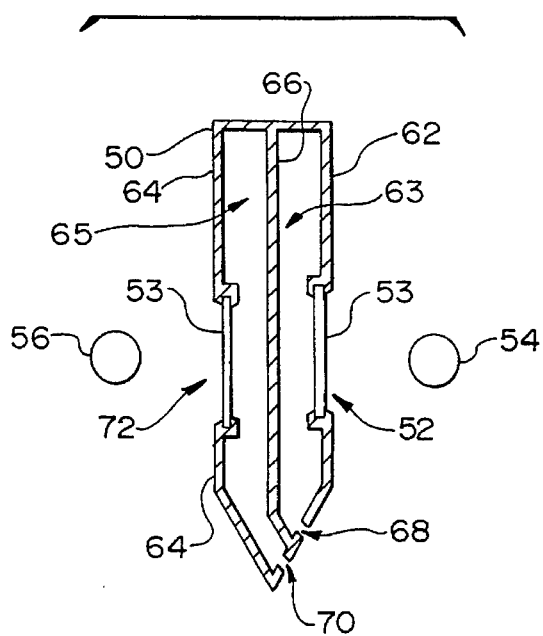

Another embodiment, shown in FIGS. 5a and 5b, uses a die 50 with die side wall fenestrations 52, 72 constructed using a transparent covering 53 mounted in outer walls 62 and 64 and made with appropriate material to allow in light from light sources 54, 56. Die 50 is set up for handling two functional coatings delivered by lines 58, 60. Die 50 is separated into two chambers 63 and 65 by a divider 66. The functional coating material supplied by lines 58, 60 are delivered to their respective chambers 63, 65. The contents of chamber 63 are extruded through die slit 68 with chamber 65 ending in die slit 70. The respective functional coatings moving through chambers 63, 65 are activated independently.

Figure 6:
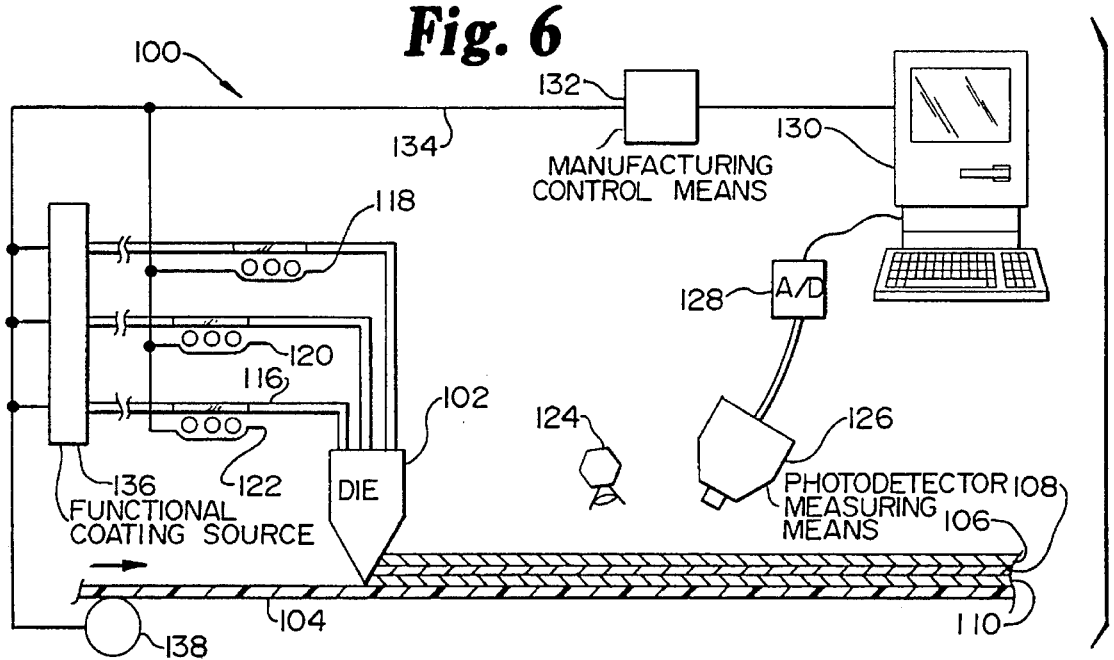
FIG. 6 is a side schematic view of an on-line embodiment of the invention.

FIG. 6 is a side schematic view of an embodiment of the present invention shown as system 100 comprising: a die 102; activation light sources 118, 120, and 122; an excitation light source 124; photodetector measuring means 126; an analog to digital (A/D) signal demodulator 128; calculating means 130; coating manufacturing control means 132; feedback control means 134; functional coating source 136; and web speed control means 138. As shown in FIG. 6, die 102 is arranged to receive three separate functional coatings from source 136 through lines 112, 114, and 116. Activation light sources 118, 120, and 122 are physically arranged to limit the output of each light source 118, 120, and 122 to the adjacent respective functional coating lines 112, 114, and 116. Light sources 118, 120, and 122 are independently controllable allowing for independent activation of each functional coating by light directed through the appropriately transparent walls of lines 112, 114, and 116 of similar construction as shown by transparent walls 36 and 38 of FIG. 4.

One possible sequence of operation of system 100 is the following. Each functional coating is mixed with a photoisomer, for example BIPS, in a known amount. Next, activation light source 118 emits a light having a wavelength range in the inducing wavelength range A of the photoisomer used in order to activate the photoisomer in the functional coating carried in line 112 to die 102. Die 102 layers all of the functional coatings onto moving thin film web 104. For example, the functional coating liquid delivered through line 112 is layered as functional coating layer 106. The activated photoisomer in functional coating layer 106 is excited by excitation light from excitation light source 124 emitting light in the absorption wavelength range B for the photoisomer used. Photodetector measuring means 126 is adjusted to detect and measure the intensity of the light emitted by fluorescence of the excited photoisomer. Photodetector measuring means 126 may include a monochromator with a diffraction grating or a suitable filter, or other similar means in conjunction with a photodetector such as a photomultiplier tube. A signal proportional to the intensity of fluorescence of the photoisomer is sent from photodetector measuring means 126 to a signal demodulator 128 for conversion into a signal usable by calculating means 130. Calculating means 130 includes such devices as a programmable computer. Calculating means 130 is programmable to provide a functional characteristic value of functional coating layer 106. This functional characteristic value may be in the form of a coating layer thickness value, a coating layer weight value, a measure of coating layer curing, or some other functional characteristic measurable by the present invention.

System 100 is capable of sequentially measuring, each functional coating. After measuring the functional characteristic of functional layer 106, the remaining functional layers 108 and 110 may be measured in turn by turning off activation light source 118 and turning on one of the remaining activation light sources, such as activation light source 120 or 122. Which light source is activated is dependent on the particular use intended for system 100. As the activated photoisomer in the functional coating liquid in line 112 clears die 102, the next functional coating liquid, for example a functional coating liquid carried in line 114 may be activated by activation light source 70. The functional coating liquid with activated photoisomer delivered through line 114 is spread onto thin film web 104 as functional coating layer 108. The measuring and calculating steps are the same. In this way system 100 switches back and forth among the layers 106, 108, and 110, measuring each layer in turn as the manufacturing process continues.

The functional characteristic value calculated by calculating means 130 may be further used by control means 132 to control the conditions of manufacture. Control means 132 may use feedback control means 134 to control conditions of manufacture within user set control parameters as part of a product quality assurance program. Examples of manufacturing parameters that are amenable to control are layer thickness and curing rates, or fluid pressures, temperatures or flow rates in source 136 or feeding lines 118, 120, and 122 to die 102, or web 104 speed control 138.

Figure 7:
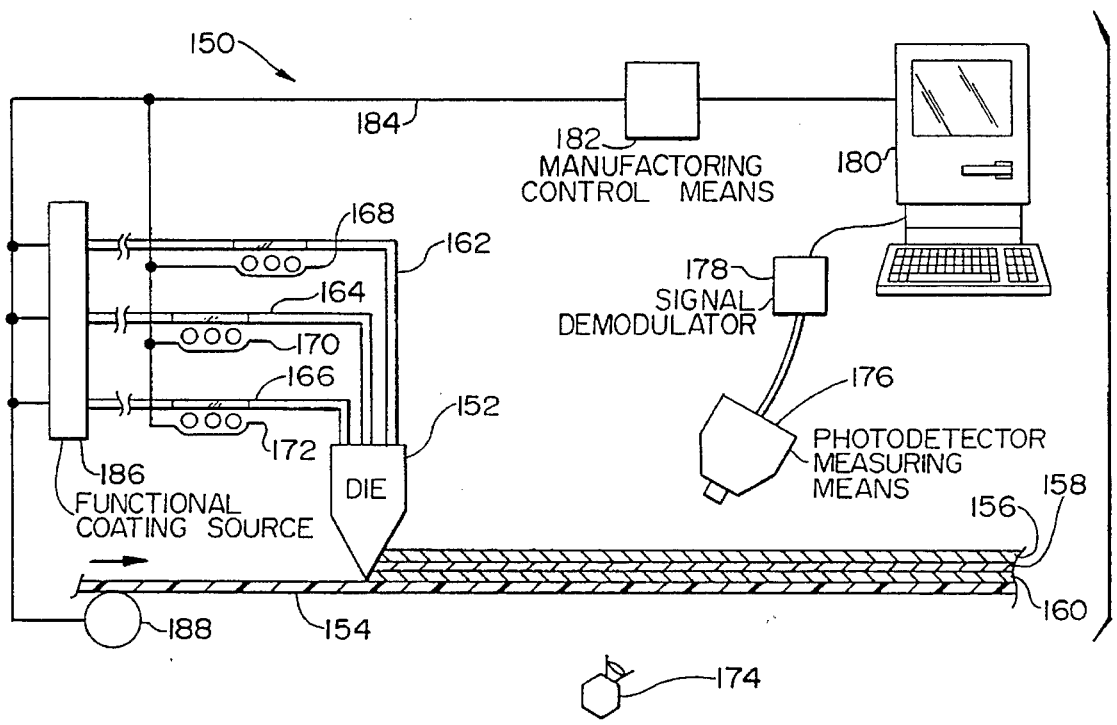
FIG. 7 is a side schematic view of another on-line embodiment of the invention.

FIG. 7 depicts another embodiment, system 150, of the present invention taking advantage of the absorption wavelength range B in an activated photoisomer. System 150 in FIG. 7 comprises: a die 152; activation light sources 168, 170, and 172; a light source 124 providing light in the absorption wavelength range B of the photoisomer chosen for use, for example BIPS; photodetector measuring means 176; an analog to digital (A/D) signal demodulator 178; calculating means 180; control means 182; feedback control means 184; functional coating source 186 and web speed control 188.

Figure 2:
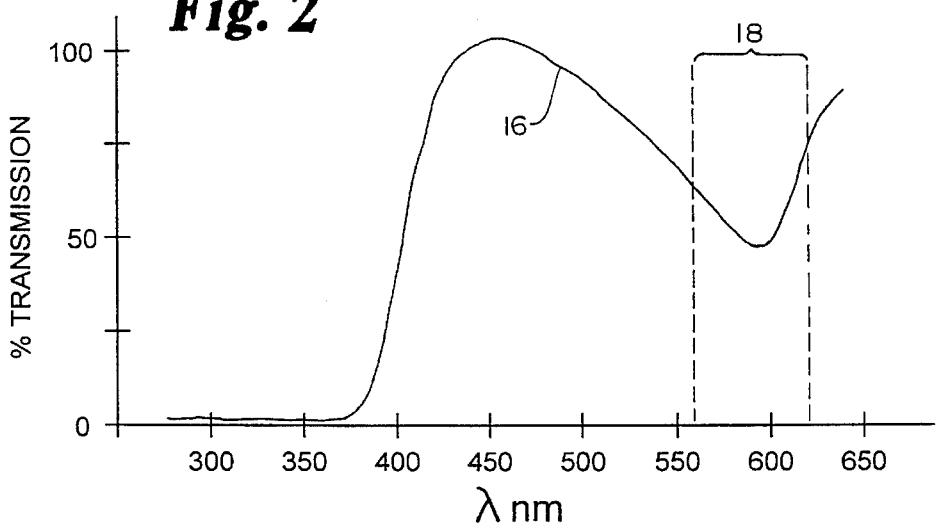
FIG. 2 is a graphic representation of a light transmission spectrum curve for the photoisomer 1,3',3'-trimethyl-6'-nitrospiro-(2-H'-1'-benzopyran-2-2'-indoline) (BIPS) in the activated state.

Functional coating liquids, each containing a photoisomer probe in a known amount, are delivered to die 152 through lines 162, 164, and 166 from functional coating source 186. Each line 162, 164, and 166 have transparent walls opposite their respective activation light sources 168, 170, and 172 of similar construction as depicted by transparent walls 36 and 38 from FIG. 4. Light sources 168, 170, and 172 are independently controlled, and by using appropriate shielding, activate only the photoisomer probe contained within the functional coating liquid carried in the line adjacent to the light source. Die 152 layers each of the functional coating liquids simultaneously as functional coating layers 156, 158, and 160 onto thin film web 154 in the manufacturing process. System 150 activates the photoisomer probe within only one functional coating at a time. When that functional coating appears as a layer on thin film web 154, it passes through a beam of light emitted from light source 174. The wavelength range of light source 174 is chosen to correspond to the Δ-absorption wavelength range B of an activated photoisomer, such as BIPS which is depicted in FIG. 2. The amount of absorption, or decrease in light transmission is detected and measured by photodetector measuring means 176 set to detect and measure the wavelength of light emitted by light source 174. Photodetector measuring means 176 may include a monochromator with a diffraction grating or a suitable filter, or other similar means in conjunction with a photodetector such as a photomultiplier tube. The signal from photodetector measuring means 176 is sent to signal demodulator 178 and converted into a digital signal useful to calculating means 180. Calculating means 180 includes such devices as a programmable computer. Calculating means 180 calculates a functional characteristic value for the functional coating layer based on the degree of absorption, or decrease in light transmission detected as a result of the activated photoisomer probe. System 150 may also have additional manufacturing control means 182 to control the conditions of manufacture to ensure proper parameters of manufacturing. The functional characteristic value calculated by calculating means 180 may be further used by control means 182 to control the conditions of manufacture. Control means 182 may use feedback control means 184 to control conditions of manufacture within user set control parameters as part of a product quality assurance program. Examples of manufacturing parameters that are amenable to control are layer thickness and curing rates, or fluid pressures in source 186 or feeding lines 168, 170, and 172 to die 152, or web 154 speed control 188.

FIG. 8 depicts another embodiment of the present invention as a system 200 using the deactivation characteristics of photoisomers to allow simultaneous use of a plurality of functional characteristic measuring stations. System 200 comprises: dies 202, 204, and 206; activation light sources 214, 216, and 218; excitation light sources 228, 234, and 240; photodetector measuring means 230, 236, and 242; deactivating means 232, 238, and 244; an analog to digital (A/D) signal demodulator 246; and calculating means 248. All light sources, detection means and deactivation means are appropriately shielded to allow use of the invention. Although not depicted, system 200 could also comprise manufacturing control means for controlling the manufacturing process for layering functional coatings onto thin film webs, as shown representatively in FIGS. 6 and 7.

As shown in FIG. 8, die 202 receives a functional coating liquid through line 208. A fluorescing photoisomer, such as BIPS, has been mixed into the functional coating in a known amount. Line 208 has an appropriately transparent wall opposite activation light source 214 allowing activation of the photoisomer within line 208 by light emitted from activation light source 214. Die 202 layers the functional coating material received from line 208 onto moving thin film web 220 as a functional coating layer 222.

The activated photoisomer within functional coating layer 222 is excited by excitation light source 228 emitting light in the Δ-absorption wavelength range B for the photoisomer used. The excitation of the photoisomer results in fluorescence of the photoisomer which is detected by photodetector measuring means 230. Photodetector measuring means 230 may include a monochromator with a diffraction grating or a suitable filter, or other similar means in conjunction with a photodetector such as a photomultiplier tube. Photodetector measuring means 230 generates a signal corresponding to the intensity of fluorescence measured which is then sent to signal demodulator 246, converting the signal into a digital signal for use by calculating means 248. Calculating means 248 may include a computer and calculates a functional characteristic value proportional to the measured fluorescence intensity of the activated photoisomer, described above.

The activated photoisomer is subsequently deactivated by deactivation means 232. Deactivation means 232 may include a light source emitting light in the Δ-absorption wavelength range B appropriate for the photoisomer and of sufficient intensity to accomplish full deactivation. Deactivation means 232 may also include a heat source of sufficient temperature to completely deactivate the photoisomer used. The use of heat is particularly practical because many functional coatings are cured through the process of heating. Another deactivation means comprises supplying sufficient energy of a type appropriate to accomplish irreversible destruction of the photoisomer. The deactivation step turns off the photoisomer in functional coating layer 222 to prevent the photoisomer in layer 222 from interfering with any further measurements.

The deactivated photoisomer of layer 222 will not interfere with any subsequent measuring steps even if the same photoisomer, such as BIPS, is used in those subsequent steps. As shown in FIG. 8, die 204 delivers a functional coating liquid received from line 210 as a functional coating layer 224 onto thin film web 220 and layer 222. If the same photoisomer, for example BIPS, is used in functional coating layer 224 as was used in coating layer 222, then because the photoisomer is activated while still in line 210 by activation light source 216, there will not be any reactivation of the deactivated photoisomer present in layer 222. Light from excitation light source 234 will cause fluorescence only from activated photoisomer, which is found in layer 224. Photodetector measuring means 236 measures the intensity of the fluorescence and sends a signal equivalent to that intensity to signal demodulator 246 and to calculating means 248 to arrive at a functional characteristic value for layer 224. The photoisomer present in layer 224 is deactivated as thin film web 220 moves past deactivation means 238.

As shown in FIG. 8, system 200 repeats the process a third time, although any number of measurement sequences can be used for any number of layers produced, using one or more photoisomers depending on the results sought for. The third sequence depicted in FIG. 8 uses die 206 to layer a functional coating liquid, from line 212, as a functional coating layer 226 onto thin film 220. The photoisomer has been added to the liquid functional coating in a known amount and is activated by light emitted from activation light source 218. Fluorescence is induced by light from excitation light source 240 and the intensity of the fluorescence is detected and measured by photodetector measuring means 242. A signal representative of the fluorescent intensity is sent to demodulator 246 where the signal is converted to a binary format for use by calculating means 248 to calculate a functional characteristic value.

Use of this invention permits on-line manufacturing measurement of functional characteristics for thin film functional coatings applied to thin film webs. The process used in this invention is nondestructive to the material being manufactured and is sufficiently fast to allow real time feedback control of the manufacturing process. The invention is versatile in allowing adaptation for use of virtually any number and type of photoisomer based on the needs of the user and considering photoisomer characteristics, including but not limited to characteristics such as light absorption, activation, deactivation, fluorescence, light wavelength ranges, solubility, and chemistry to list a few.

We claim:

1. A method for measuring a functional characteristic of one or more functional coatings applied to a film layer, comprising the steps of:

mixing each functional coating with a known amount of a photoisomer, the photoisomer having a light inducing wavelength range A, and when activated has an excitation wavelength range B and a fluorescent light emissions wavelength range C;

activating the photoisomer in each functional coating sequentially with light from wavelength range A;

coating a film layer with each functional coating;

exciting the photoisomer in each functional coating with light from wavelength range B;

measuring light fluorescence in wavelength range C of each functional coating in response to being excited by light of wavelength range B; and calculating a functional characteristic value for each functional coating based on the measured fluorescence.

2. The method of claim 1 further comprising the step of controlling a functional coating manufacturing process depending on the functional characteristic value.

3. The method of claim 1 further comprising the step of deactivating the photoisomer after measuring the fluorescence.

4. The method of claim 3 in which the deactivating step comprises deactivating the photoisomer with heat.

5. The method of claim 3 in which the deactivating step comprises deactivating the photoisomer with light from wavelength range B.

6. The method of claim 1 in which the mixing step comprises mixing a different photoisomer for each functional coating applied to the film layer; each different photoisomer having its own wavelength ranges A, B and C such that activating each photoisomer uses the appropriate wavelength range A, exciting each photoisomer uses the appropriate wavelength range B and the measuring of fluorescence is in the appropriate wavelength range C for each photoisomer used.

7. A system for measuring a functional characteristic of one or more functional coatings applied to a film layer, comprising:

a photoisomer, with a known amount of the photoisomer mixed into each functional coating prior to applying the functional coating to the film layer, the photoisomer being capable of activation by a light in a wavelength range A, and when activated being capable of excitation by light from a wavelength range B and emitting fluorescence of light in a wavelength range C;

a radiant light source of wavelength A for sequentially activating the photoisomer;

a radiant light source of wavelength range B for exciting the photoisomer in each functional coating applied to the film layer;

fluorescent measuring means for measuring the fluorescence of light in wavelength range C emitted by the photoisomer; and calculating means for calculating a functional characteristic value for each functional coating.

8. The system of claim 7 further comprising control means for controlling a functional coating manufacturing process using the functional characteristic value as a parameter for controlling the application of each of the functional coatings.

9. The system of claim 7 further comprising photoisomer deactivating means for deactivating the photoisomer so that the photoisomer is no longer capable of excitation by light in wavelength range B and does not appreciably fluoresce light in wavelength range C.

10. The system of claim 9 in which the deactivating means comprises a radiant light source in wavelength range B.

11. The system of claim 9 in which the deactivating means comprises a source of heat for heating the photoisomer.

12. The system of claim 7 further comprising a plurality of photoisomers, each photoisomer having its own wavelength ranges A, B and C, a different photoisomer being mixed into each functional coating prior to applying the functional coating to the film layer.

* * * * *